(12) United States Patent
Nimmo

(10) Patent No.: US 11,998,210 B2
(45) Date of Patent: Jun. 4, 2024

(54) SURGICAL DEVICE

(71) Applicant: VASCUTEK LIMITED, Renfrewshire (GB)

(72) Inventor: Seonaid Barbara Nimmo, Strathclyde (GB)

(73) Assignee: VASCUTEK LIMITED, Renfrewshire (GB)

(*) Notice: Subject to any disclaimer, the term of this patent is extended or adjusted under 35 U.S.C. 154(b) by 370 days.

(21) Appl. No.: 17/209,414

(22) Filed: Mar. 23, 2021

(65) Prior Publication Data

US 2021/0204954 A1 Jul. 8, 2021

Related U.S. Application Data

(63) Continuation of application No. PCT/GB2019/052533, filed on Sep. 11, 2019.

(30) Foreign Application Priority Data

Sep. 25, 2018 (GB) .................................... 1815630

(51) Int. Cl.
*A61B 17/12* (2006.01)
*A61B 17/00* (2006.01)

(52) U.S. Cl.
CPC .................. *A61B 17/12009* (2013.01); *A61B 2017/00862* (2013.01)

(58) Field of Classification Search
CPC ........ A61B 17/12009; A61B 17/12013; A61B 17/122; A61B 17/1227; A61B 17/1327;
(Continued)

(56) References Cited

U.S. PATENT DOCUMENTS

| | | | | |
|---|---|---|---|---|
| 4,988,355 A | * | 1/1991 | Leveen | A61B 17/12009 606/151 |
| 5,888,188 A | * | 3/1999 | Srougi | A61F 2/0036 128/DIG. 25 |

(Continued)

FOREIGN PATENT DOCUMENTS

| | | |
|---|---|---|
| DE | 2402677 A1 | 7/1975 |
| WO | 9701309 A1 | 1/1997 |

(Continued)

OTHER PUBLICATIONS

International Search Report and Written Opinion of the International Searching Authority for International Application No. PCT/GB2019/052533 dated Nov. 21, 2019.

*Primary Examiner* — Kathleen S Holwerda
*Assistant Examiner* — Serenity A Miller
(74) *Attorney, Agent, or Firm* — Stephen J. Kenny; Foley Hoag LLP

(57) ABSTRACT

A surgical device controls fluid flow through a vessel by releasable constriction of the vessel using a compressible "C"-shape operating member with first and second elongate flexible members respectively configured to form a first loop and a second loop, the first and second loops intersecting to define an eye surrounding the vessel, wherein the operating member has first and second arms separated by a gap, the first arm being attachable to the first elongate flexible member, the second arm being attachable to the second elongate flexible member, so as to apply tension to the first and second elongate flexible members, the eye being located in the gap, whereby compression of the operating member relaxes tension in the elongate flexible members permitting opening of the eye and fluid flow within the vessel.

9 Claims, 5 Drawing Sheets

(58) Field of Classification Search
CPC .............. A61B 17/132; A61B 17/1322; A61B 2017/081; A61B 17/083; A61B 17/0401; A61B 17/0466
USPC ................................................ 606/157, 158
See application file for complete search history.

(56) References Cited

U.S. PATENT DOCUMENTS

2005/0256365 A1   11/2005  Timm et al.
2009/0259093 A1*  10/2009  Bhat .................... A61F 2/0036
                                                             600/31

FOREIGN PATENT DOCUMENTS

WO      WO-9701309 A1   1/1997
WO         0176487 A1  10/2001

* cited by examiner

SURGICAL DEVICE

CROSS REFERENCE TO RELATED APPLICATIONS

This application claims priority benefit from International Application No. PCT/GB2019/052533 filed on Sep. 11, 2019, which claims priority from Great Britain Application No. 1815630.7 filed on Sep. 25, 2018, each of which is incorporated herein by reference in its entirety.

FIELD OF THE INVENTION

This invention relates to surgical devices for controlling fluid flow through a vessel defining a lumen. Natural vessels defining a lumen enabling fluid flow in physiological functioning systems and organs include tubular connective tissues of the vasculature, lymphatic system, renal system, respiratory system, etc. Synthetic or prosthetic devices also include tubular parts through which control of fluid flow is desirable during at least part of a surgical procedure. The present disclosure is applicable to both natural and synthetic vessels having a length and a transverse dimension defining a lumen or through passage, which vessels may be flexible walled vessels which can be closed to through-flow by a clamp for example.

BACKGROUND OF THE INVENTION

Commercially available valves for providing haemostasis in endovascular delivery systems are considered by many to be unduly expensive and tend to be over-engineered. Over time these valves have been found to lose their efficacy and the ability to provide haemostasis for example is lost.

Surgical sutures, loops or ligatures are currently used for constricting or ligating natural vessels during surgery. An arrangement comprising a wire-like surgical loop with a holding member is disclosed in WO 01/76487. However, to loosen and tighten these surgical loops has been found to be awkward and time consuming during a surgical procedure, when efficient use of time is crucial.

It is an object of the present invention to mitigate or obviate at least one problem with prior devices and provide a device which is simple in design and easy to use.

SUMMARY OF THE INVENTION

According to a first aspect of the present invention, there is provided a device for controlling fluid flow through a vessel defining a lumen through which fluid may flow, comprising:

at least one elongate flexible member configured to form an eye for surrounding the vessel defining a lumen, the at least one elongate flexible member having a first attachment point and a second attachment point; and an operating member for mounting the at least one elongate flexible member, which has at least first and second arms respectively extending from a common point which may be a handle, or joint, and in preferred embodiments the operating member may be configured as substantially C-shaped, V-shaped or U-shaped, or the like. The first arm of the operating member may be attachable to the first attachment point of the at least one elongate flexible member, and the second arm of the operating member may be attachable to the second attachment point of the at least one elongate flexible member. The operating member is sized for a user to manipulate the operating member in one hand, so as to provide a handheld device for mounting the at least one elongate flexible member.

In embodiments, the operating member may be formed from a flexible material with sufficient resilience to provide tension in the at least one elongate flexible member when required, whilst allowing a user to manipulate the operating member to reduce the tension in the at least one elongate flexible member when required. The common point of the operating member may be a flexure to provide for relative movement of the first and second arms of the operating member or a spring biased hinge portion. The material selected for the operating member, particularly the flexure provides for recoverable strain without permanent deformation.

In embodiments where the, or alternatively, each elongate member is selected from materials known to be relatively highly flexible, for example silicone rubber cord, the person skilled in the art will understand and give due consideration to material parameters for the elongate flexible member including tensile modulus (in GPa) and recoverable tensile strain (%). Both of these properties can be measured for the elongate flexible member using a uniaxial tensile stress-strain test (e.g. according to ASTM D 412, ASTM D638, or optionally ASTM D1708), where the elongate member sample is loaded in tension to a certain maximum deflection and unloaded. In this case, typical suitable modulus range for the 'flexible' elongate member would be from 0.01 to 0.1 GPa and typical suitable recoverable strain would be from 5% to 300%. However, these are only example ranges, and further embodiments are contemplated where the elongate flexible member has properties outside this range (for example, an elongate member of material with higher modulus and lower recoverable strain but with different cross-sectional/length geometry). In this case, embodiments are also contemplated where the elongate flexible member comprises a polymer or metal/alloy wire or braid.

In this case using such a flexible elongate member with relatively low tensile stiffness and high recoverable strain properties means that the 'eye' can be enlarged by extension of the elongate member material with relatively low force (for example, by insertion of a larger catheter over a guidewire within the vessel, while maintaining haemostasis), and that this extension will not result in permanent deformation of the elongate member.

For the case where the elongate member is chosen to be relatively stiff in tension (e.g. monofilament or multifilament suture, nylon or polyethylene based braided string) the key material parameter is tensile stiffness. In this case, the stiffness should be sufficiently high that there is negligible extension of the elongate member under the forces involved for achieving the haemostatic seal. In terms of the materials used in this case, they may be polymers with Young's modulus in the range of 1 to 10 GPa.

However, other materials with a different modulus could be chosen to give an elongate member design with sufficient tensile stiffness.

In this case, the elongate member's relative tensile stiffness means that the size of the 'eye' is controlled in use primarily by the position of the compressible operating member (i.e. compression upon the arms enables a user to enlarge the eye, and release of the arms allows the elongate flexible members to recover and thereby to reduce eye diameter).

In an embodiment, the compressible operating member is attachable to the first attachment point and the second attachment point of said at least one elongate flexible member, at least one arm of the compressible operating member being compressible upon the application of pressure to the compressible operating member, and operable to act upon the at least one elongate flexible member such that: the at least one elongate flexible member is movable from a first position in which the at least one elongate flexible member is under tension such that the eye constricts fluid flow within the lumen, and a second position in which the at least one elongate flexible member is relaxed such that the eye does not constrict fluid flow through the lumen.

The application of pressure to the compressible operating member may be that of finger pressure of a user of the device. The device is conveniently hand-held by a user, and pressure may be applied by compression of the compressible operating member of the device between a thumb and one or more fingers of the user.

The compressible operating member may comprise first and second arms respectively extending from a common point such as a hinge, joint, or flexible portion such that the compressible operating member may be configured as substantially C-shaped, V-shaped or U-shaped, or the like, with spaced apart free ends which are movable one towards the other when compressed by a user. The first and second arms may individually have straight or curved length parts. The first and second arms may be made from a resilient form-retaining material such that when a user releases the first and second arms from a compressed state, the first and second arms return to their original configuration. The uncompressed state may be considered as a first configuration wherein the elongate flexible member is in a first position. The compressed state may be considered as a second configuration wherein the elongate flexible member is in a second position.

The device may incorporate a configuration biasing member to ensure that the first and second arms return to the uncompressed first configuration after a user has compressed and released the compressible operating member. The configuration biasing member may be a spring such as a coil spring, leaf spring, torsion spring or the like arranged between the first and second arms in a space of sufficient width to avoid interference with the at least one elongate flexible member, optionally at or near the hinge, joint, or flexible portion of the compressible operating member to bias the first and second arms towards the uncompressed first configuration. The use of such a configuration biasing member may also be beneficial in maintaining or countering tension in the at least one elongate flexible member.

In embodiments where the operating member is of a less flexible or of a stiffer material which is more resistant to compression by hand or finger pressure of a user, the at least one elongate flexible member may be an elongate resilient member retaining elastic properties under tension. The elongate resilient member would exhibit limited elongation under tensile loads, but return to its original length when loading is removed. Whilst under tensile load the elongate resilient member would exhibit resistance to further elongation or "creep".

Whereas, natural fibers such as silk or cotton may be used alone or coated to modify the natural properties thereof, a flexible silicone material may be suitable for the at least one elongate flexible member. The at least one elongate flexible member may be a synthetic filament which filament may be optionally silicone-coated, or at least partially PTFE-coated, which filament may be based on a nylon, a polyester, polypropylene, polyvinylidene fluoride (PVDF) or another flexible material of similar physical properties that is easily manipulated and shaped but is not permanently stretched under tension as contemplated for the disclosed use when attached to the compressible operating member.

The at least one elongate flexible member is intended to provide a readily manipulated mechanism that is user-initiated to shift from a lumen occluded condition to a lumen open condition, but it will be understood that a user may grip and manipulate the elongate flexible member through positions intermediate the first position and second position.

The "vessel" may be a natural vessel such as a blood vessel. Alternatively, the "vessel" may be a synthetic vessel such as a branch of a vascular graft. The "elongate flexible member" should be understood to be an elongate flexible member capable of being readily formed into at least one loop to define an internal space within the loop which is referred to herein as "an eye". The elongate flexible member may be for example a strand, thread, filament, ribbon, fibre or cord, or a piece of string, the internal space within the loop being adapted to receive the width of the vessel. The elongate flexible member may be easily manipulated and shaped, and resilient but may not be stretched under tension beyond the elastic limits of the material from which the elongate flexible member is made in the disclosed use when attached to the compressible operating member.

In the case of application to a prosthetic device having soft fabric tubular portion, it will be understood that closure of the eye around the soft fabric tubular portion of the prosthetic device permits a conformable seal around any object presented within the soft fabric tubular portion of the prosthetic device. Thus, it is thereby possible to provide a haemostatic seal, whilst permitting passage of any object such as a catheter, wire, or other typical delivery system component through the soft fabric tubular portion of the prosthetic device if required. In this way the disclosed device acts as a readily applied and removable haemostatic valve. Optionally the device may be tethered to the graft to keep it in position during the surgical procedure.

The operating member may be operable to act on the at least one elongate flexible member such that the at least one elongate flexible member is biased towards the first position.

The operating member may be a bifurcated device such as a "C"-shaped member, or V-shaped or U-shaped, or similar configuration having first and second arms separated by a gap. The first arm of the operating member may be attachable to the first attachment point of the at least one elongate flexible member, and the second arm of the operating member may be attachable to the second attachment point of the at least one elongate flexible member. The at least one elongate flexible member may be manipulated to form at least one loop defining the eye before attachment to the operating member. The eye may be located in the gap between the first and second arms of the operating member. At least one of the first and second arms of the operating member may be movable inwardly relative to the other of the first and second arms of the operating member, so as to move the at least one elongate flexible member from the first position to the second position. The first and second arms may each have an aperture through which the at least one elongate flexible member may be passed and attached to the respective arm in an assembly step prior to use. The aperture respectively in each of the first and second arms may be accessible from above and below the arm, i.e. an aperture which is circular or oval, or additionally accessible through a side slot, for example an aperture which when viewed from above the arm is substantially J-shaped, or substantially L-shaped. The apertures may form part of an attachment structure for example to serve as a threading arrangement for attachment of the at least one elongate flexible member.

In an embodiment at least one aperture through which the at least one elongate flexible member may be passed may be a pinhole aperture in at least one of the first and second arms of the operating member. The pinhole aperture may be defined by a surface configured such that at least a portion of the at least one elongate flexible member interacts with the surface upon contact therewith such that friction between the surface and the contacting portion of the at least one elongate flexible member acts to locate the at least one elongate flexible member sufficiently without additional fastening means. The pinhole aperture-defining surface may be roughened, ribbed, grooved, or serrated to increase frictional interaction with the at least one elongate flexible member. Thereby the at least one elongate flexible member can be suitably positioned and configured for use, yet avoid undesirable loosening or slackening in use. Preferably each of the first and second arms is provided with such a pinhole aperture. A user can selectively alter the configuration, for example to enlarge the "eye" by applying sufficient force to a portion of the at least one elongate flexible member to overcome friction between the contacting portion of the at least one elongate flexible member and the pinhole aperture-defining surface.

In an embodiment the operating member and the at least one elongate flexible member are pre-assembled to provide a user with a "ready for use" device for controlling fluid flow through a vessel defining a lumen through which fluid may flow. In such an embodiment the at least one elongate flexible member is threaded through the apertures and pulled through by a length sufficient to form a loop defining an eye of a desired size.

The at least one elongate flexible member may be made from a material which has a reduced tendency to slip through the aperture absent a user applied pull of sufficient force to overcome friction between the contacting portion of the at least one elongate flexible member and the pinhole aperture-defining surface. A flexible silicone material may be suitable for the at least one elongate flexible member. At least a portion of the flexible silicone material may be covered with a removable low-friction material to facilitate assembly when threading the at least one elongate flexible member through the aperture(s). Polytetrafluoroethylene (PTFE) tape may serve as the removable low-friction material. Monofilament or multi-filament braided materials may be used for the at least one elongate flexible member.

The at least one elongate flexible member may be a single elongate flexible member comprising first and second ends. The first arm of the operating member may comprise a first threading arrangement, and the second arm of the operating member may comprise a second threading arrangement. The first end may be threaded through the first threading arrangement, and the second end may be threaded through the second threading arrangement.

Each of the first and second threading arrangements may comprise an aperture which is shaped, so as to provide a plurality of winding points for the thread.

At least one, and optionally both of the first and second threading arrangements may be a transversely arranged J-slot accessible from a side of the arm of the operating member.

The at least one elongate flexible member may comprise: a first elongate flexible member configured to form a first loop; and a second elongate flexible member configured to form a second loop. The first and second elongate flexible members may be configured such that the first and second loops are juxtaposed so as to define the eye for surrounding the lumen. For example, the first and second loops may be linked together. The first elongate flexible member may comprise the first attachment point and the second elongate flexible member may comprise the second attachment point.

The first arm of the operating member may comprise a first threading arrangement, and the second arm of the operating member may comprise a second threading arrangement. The first elongate flexible member may be threaded through the first threading arrangement and the second elongate flexible member may be threaded through the second threading arrangement.

Each threading arrangement may comprise an aperture, and each elongate flexible member may extend through the aperture through the loop formed by the other elongate flexible member and back through the aperture. The aperture of each threading arrangement may be defined by a surface configured such that at least a portion of the at least one elongate flexible member interacts with the surface upon contact therewith such that friction between the surface and the contacting portion of the at least one elongate flexible member acts to locate the at least one elongate flexible member sufficiently without additional fastening or retention means. The aperture-defining surface may be roughened, ribbed, grooved, or serrated to increase frictional interaction with the at least one elongate flexible member. Thereby the at least one elongate flexible member can be suitably positioned and configured for use, yet avoid undesirable loosening or slackening in use.

The threading of the at least one elongate flexible member for attachment of the at least one elongate flexible member to the first and second arms of the operating member may be secured by tying a knot in the at least one elongate flexible member to prevent slippage through the aperture in the arm of the operating member in use.

The at least one elongate flexible member may be formed from a silicone.

The at least one elongate flexible member may be a resilient cord.

The operating member may be compressible upon the application of finger pressure.

In use of the device, especially in embodiments where the at least one elongate flexible member is in fact a single elongate flexible member, the maintenance of the eye in a dilated loop configuration whilst manipulating the device with respect to application to, or removal from, a vessel may be facilitated by insertion of an elongate keeper which may be any elongate instrument that is to hand such as a thin probe, end of a catheter, handle of a scalpel, urethral dilator, or the like.

In preferred embodiments the use of two intersecting loops of first and second elongate flexible members operable together to define an eye of variable dimensions provides that the formed eye remains available for dilation or closing about a vessel at all times.

According to a second aspect of the present invention, there is provided a prosthetic graft comprising a tubular branch defining a lumen, and a device, as defined above, for controlling fluid flow through the lumen of the tubular branch, wherein the eye of the device surrounds the branch of the graft.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

DETAILED DESCRIPTION OF THE DRAWINGS

Figure 1:
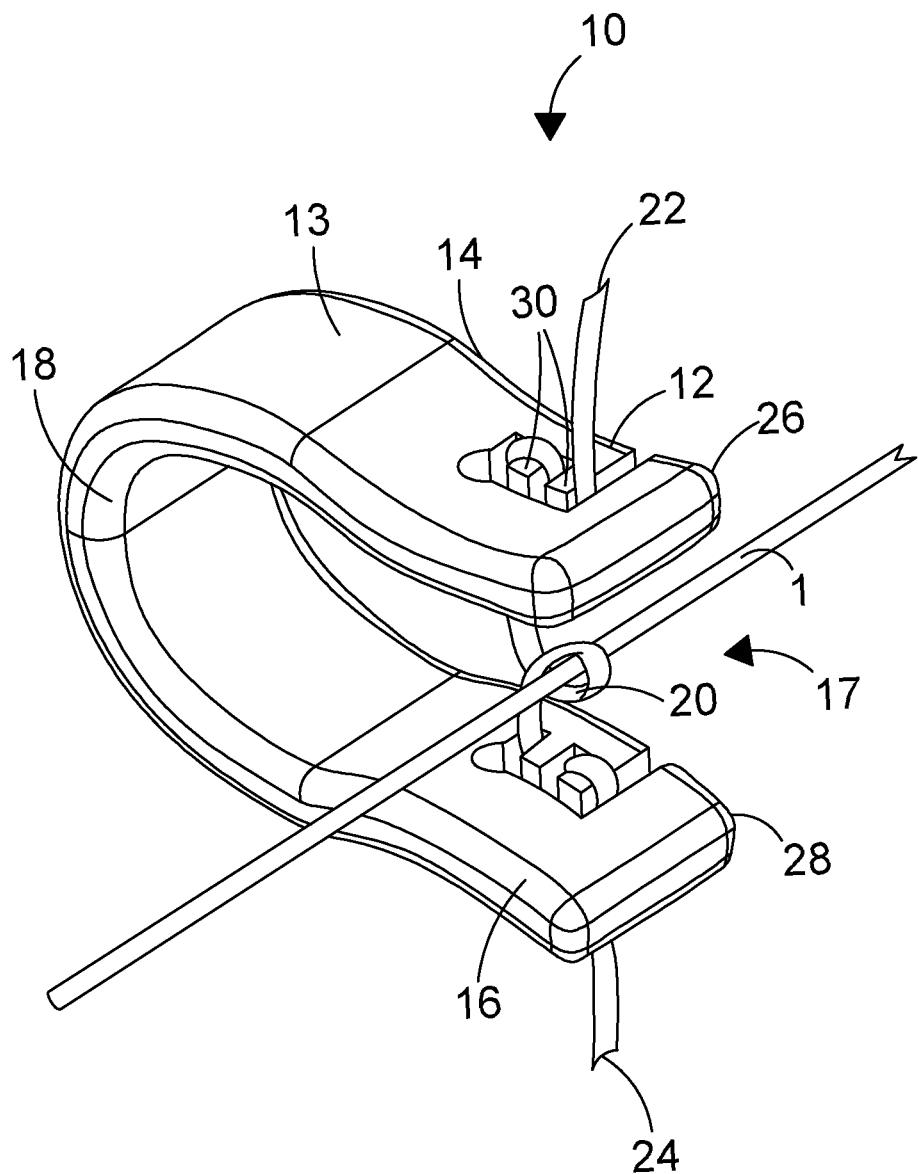
FIG. 1 is a side perspective view of a device, in accordance with an aspect of the present disclosure.

Reference is now made to FIG. 1, which shows a device 10 for controlling fluid through a vessel 1 defining a lumen, in accordance with a first embodiment of the present invention. The device 10 comprises an elongate flexible member 12, which in the depicted example is a flexible cord.

The device 10 also comprises a compressible operating member 13, which in the depicted example is a C-shaped member. The C-shaped member 13 comprises first and second arms 14, 16, having distal free ends, which are separated by a gap 17 and extend from a common point in the form of a proximal hinge portion 18 of the C-shaped member. In the depicted example, the hinge portion 18 is a flexible U-shaped portion of the C-shaped member 13. As shown in FIG. 1, the elongate flexible member 12 is configured to form an eye 20 for surrounding the vessel 1. The eye 20 is located in the gap 17 and in use may lie substantially transversely over the exterior of the vessel 1.

The terms "hinge" and "hinge portion" as used in this disclosure and claims relates to a flexible connection, joint, or return portion between proximal ends of the first and second arms of this or any embodiment whereby at least one of the first and second arms can be moved towards the other of the first and second arms.

The first arm 14 comprises a first threading arrangement 26, and the second arm 16 comprises a second threading arrangement 28. The elongate flexible member 12 is attached to the C-shaped member 13 by threading a first end 22 of the elongate flexible member through the first threading arrangement 26 and by threading a second end 24 of the elongate flexible member through the second threading arrangement 28.

In the depicted example, each of the first and second threading arrangements 26, 28 is an aperture which comprises a comb-shaped portion. Each aperture therefore forms a plurality of teeth 30 of the C-shaped member 13. In the depicted example, each end of the elongate flexible member 12 is threaded around the teeth 30 of its associated threading arrangement 26, 28. Each portion of the elongate flexible member 12 located in one of the threading arrangements 26, 28 forms a friction fit with that threading arrangement, which allows the portion of the first elongate flexible member 12 located in the gap 17 to be tensioned, and the eye to be biased towards a closed position. The elongate flexible member 12 is threaded through the threading arrangements 26, 28 such that in a rest position the portion of the elongate flexible member 12 located in the gap 17 is under tension and the eye 20 may constrict fluid flow through a lumen.

Either of the arms 14, 16 is movable inwardly in response to pressure applied to its outer surface. This means that if pressure is applied to one of the arms 14, 16, the portion of the elongate flexible member located in the gap 17 is relaxed, which has the effect of increasing the size of the eye 20, and allowing fluid flow through the lumen. Each of the arms 14, 16 is preferably movable in response to finger pressure applied thereto.

Figure 2A:
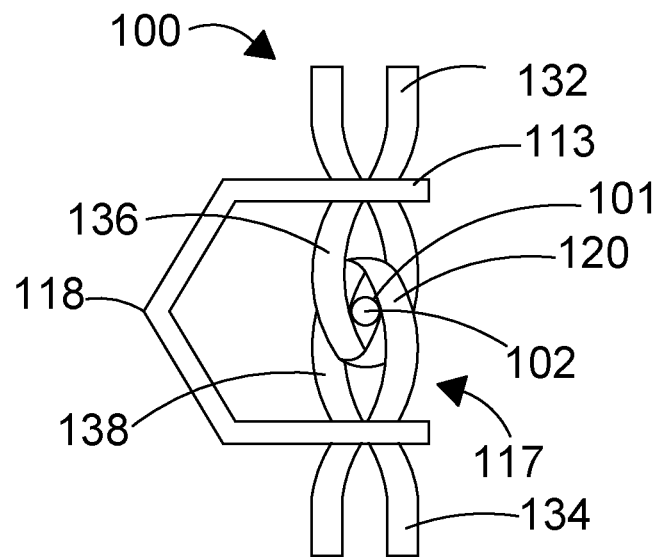
FIGS. 2A, 2B, and 2C show a second embodiment of a device, in accordance with an aspect of the present disclosure.
Figure 2B:
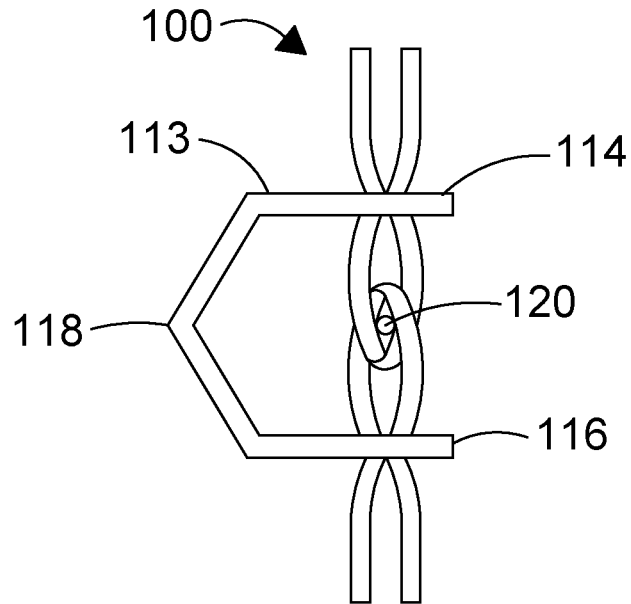
Figure 2C:
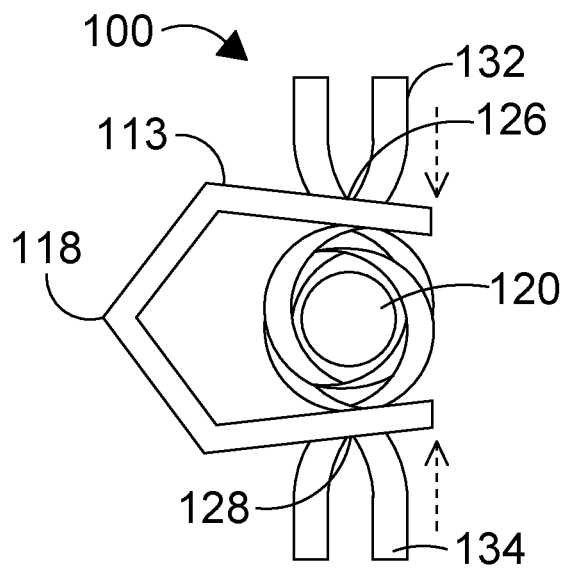

Reference is now made to FIGS. 2A, 2B and 2C, which show a device 100 for controlling fluid flow through a vessel 101 defining a lumen 102, in accordance with a second embodiment of the present invention. In the embodiment depicted, the device 100 comprises first and second elongate flexible members 132, 134. The first elongate flexible member 132 is configured to form a first loop 136, and the second elongate flexible member 134 is configured to form a second loop 138. As shown, the first loop 136 is linked with the second loop 138, so as to define an eye 120 for surrounding the vessel 101. The use of first and second elongate flexible members 132, 134 configured such that a portion of one of said first and second elongate flexible members 132, 134 passes through the loop of the other at least once to form intersecting loops, provides stability to the eye 120 so that the eye configuration is preserved even if an object such as a vessel or catheter, or surgical implement is not present within the eye. A stabilised eye is easier to use, for example, when a user wants to pass the eye over an object or insert an object into the eye. The use of intersecting loops is more advantageous than use of a single loop which may loosen and uncoil if not looped around an object.

The device 100 also comprises an operating member 113 which is operable to act upon the first and second elongate flexible members 132, 134 such that the eye 120 is reclosable. The operating member 113 in this embodiment is a C-shaped member.

In the depicted example, the operating member 113 has first and second arms 114, 116, which are separated by a gap 117 where the eye 120 is located. The first and second arms 114, 116 extend upwardly from a hinge portion 118.

Each arm 114, 116 comprises a threading arrangement 126, 128 for each elongate flexible member 132, 134. In the depicted example, each threading arrangement 126, 128 comprises a single aperture. In the depicted example, each elongate flexible member 132, 134 is threaded through its respective aperture 126, 128 into the gap 117, through the loop of the other elongate flexible member and back through its respective aperture. Each elongate flexible member 132, 134 may be a resilient cord, and sized relative to the size of its respective aperture 126, 128 such that it forms a friction fit with its respective arm inside its respective aperture. This allows the portion of each elongate flexible member 132, 134 forming the loop to be tensioned by adjusting the size of the loop.

In this embodiment both loops 136, 138 are linked with each other so that they cooperate, which has the overall effect of stabilising the eye and under tensile biasing by the operating member 113 the loops 136, 138 tend towards a rest position in which the eye 120 is closed, as shown in FIG. 2B. As shown in FIG. 2C, the arms 114, 116 are movable inwardly. This means that when a sufficient compressive force is applied to the operating member 113 such that the arms move inwardly, each of the loops 136, 138 slacken, thereby opening the eye 120.

The use of a device as disclosed herein will now be described with reference to the first embodiment described above with reference to FIG. 1. In use, the device 10 of the first embodiment may be provided such that the eye 20 already surrounds the vessel 1, if the vessel 1 is a branch of a vascular graft for example. Alternatively, the device 10 may be assembled in situ by a medical professional, as described below. When assembling the device 10, the medical professional configures the elongate flexible member 12 such that it forms the eye 20 with the vessel 1 located therein. As part of the assembly procedure, the medical professional threads the first end 22 of the elongate flexible member 12 through the first threading arrangement 26, and threads the second end 24 through the second threading arrangement 28. The medical professional then tensions the portion of the elongate flexible member 12 located in the gap 17 such that the eye constricts flow through the vessel 1. If the medical professional wishes to allow fluid through the vessel 1, the medical professional may grip the operating member and manipulate it between fingers and thumb such that simple application of finger pressure to the operating member 13, has the effect of altering the dimensions of the eye 20, changing the eye 20 into a configuration where the eye 20 opens to allow fluid flow through the vessel. As the operating member 13 biases the eye 20 towards a closed position, when the medical professional removes this finger pressure, the eye 20 returns to a tighter configuration around the vessel 1, whereby the eye 20 constricts the vessel 1 to inhibits fluid flow through the vessel.

Figure 5:
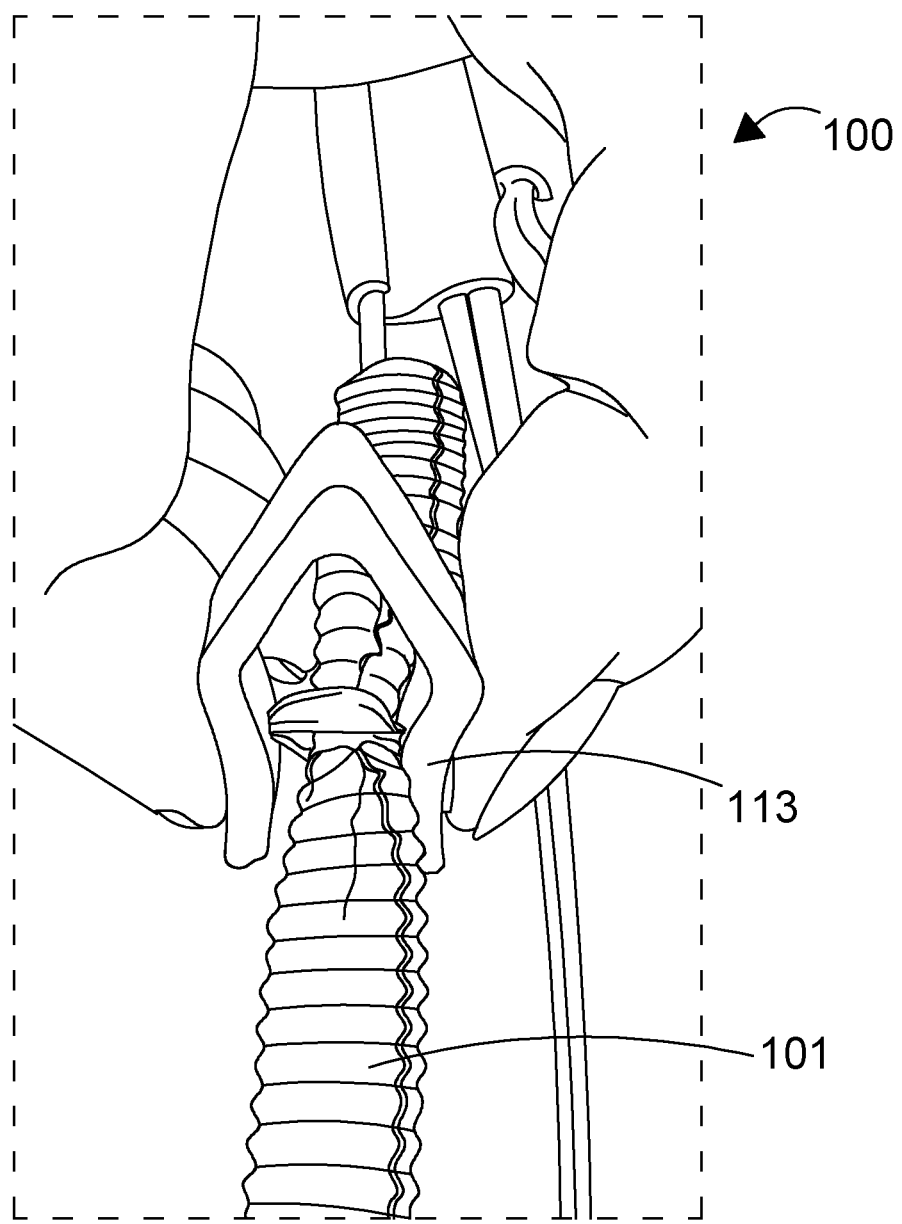
FIG. 5 shows the device of FIG. 2A in use upon a branch vessel of tubular prosthetic implant, in accordance with an aspect of the present disclosure.

The use of the second embodiment will now be described with reference to FIGS. 2A, 2B and 2C. In use, the device 100 of the second embodiment may be provided such that the eye 120 already surrounds the vessel 101, if the vessel is a tubular branch of a prosthetic device such as a vascular graft for example. Alternatively, the device 100 may be assembled in situ by a medical professional, as described below. When assembling the device 100, the medical professional configures the first and second elongate flexible members 132, 134 such that they each form a loop and are linked, so as to define the eye 120. The medical professional may do this by threading each elongate flexible member 132, 134 through its respective aperture 126, 128 into the gap 117, and one of the elongate flexible members 132, 134 through the loop of the other elongate flexible member and back through its respective aperture 126 or 128. The medical professional then tensions each of the elongate flexible members such that the eye constricts fluid flow through the vessel. With reference to FIG. 5, when the medical professional wishes to allow fluid flow through the vessel, the medical professional may grip the operating member and manipulate it such that simple application of pressure to the operating member 113, has the effect of moving the eye into a position where it allows fluid flow through the vessel 101. As the operating member 113 biases the eye towards a closed position, when the medical professional removes this pressure, the eye returns to a position where it prevents fluid flow through the vessel 101.

A further embodiment which is commercially attractive due to its relative lack of complexity, and which offers an advantage of predictable reliability in use, will now be described referring to FIGS. 3A, 3B, and 3C, together with FIG. 4.

Figure 3A:
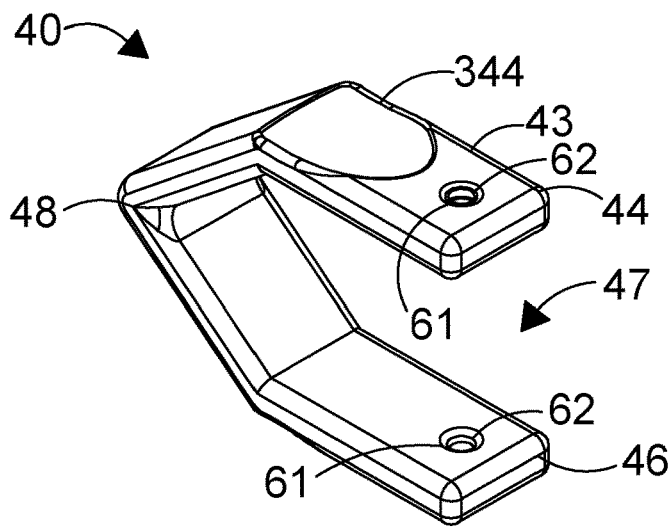
FIG. 3A shows a perspective view of a compressible operating member of generally C-shape which forms part of a manually controlled fluid flow device, in accordance with an aspect of the present disclosure.
Figure 3B:
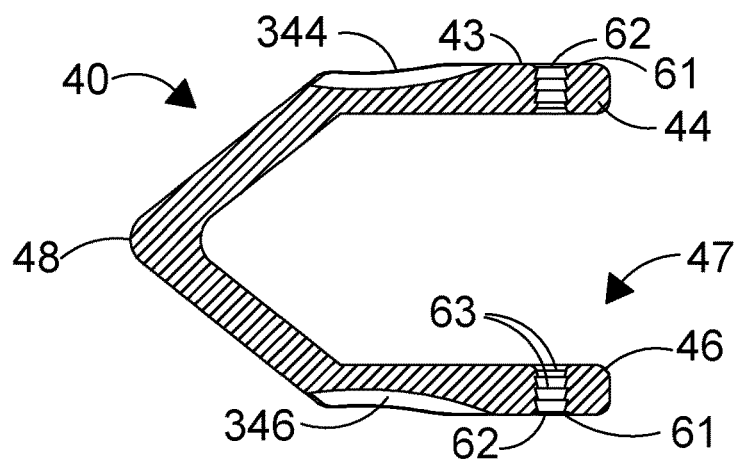
FIG. 3B shows a longitudinal side sectional view through the compressible operating member shown in FIG. 3A and illustrating upper surface and lower surface exterior indentations for a user's finger to facilitate compression of the operating member in use, in accordance with an aspect of the present disclosure.
Figure 3C:
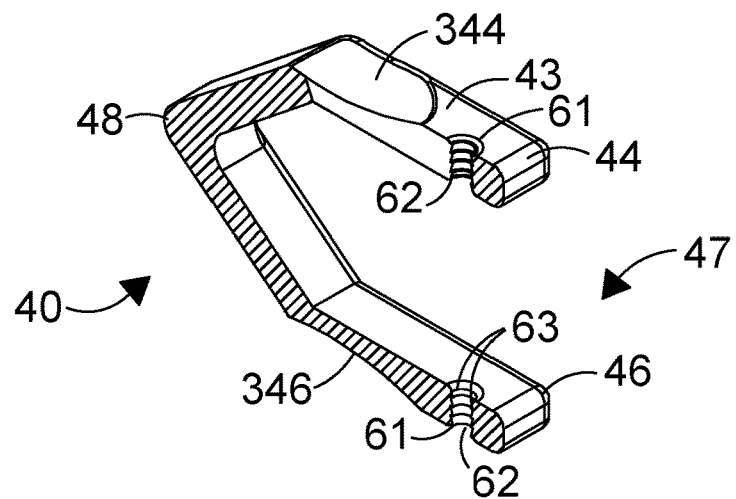
FIG. 3C shows a perspective side sectional view through the compressible operating member shown in FIG. 3A from above and to one side to illustrate more clearly the ribbed inner surface of each threading aperture for receiving an elongate flexible member, in accordance with an aspect of the present disclosure.
Figure 4:
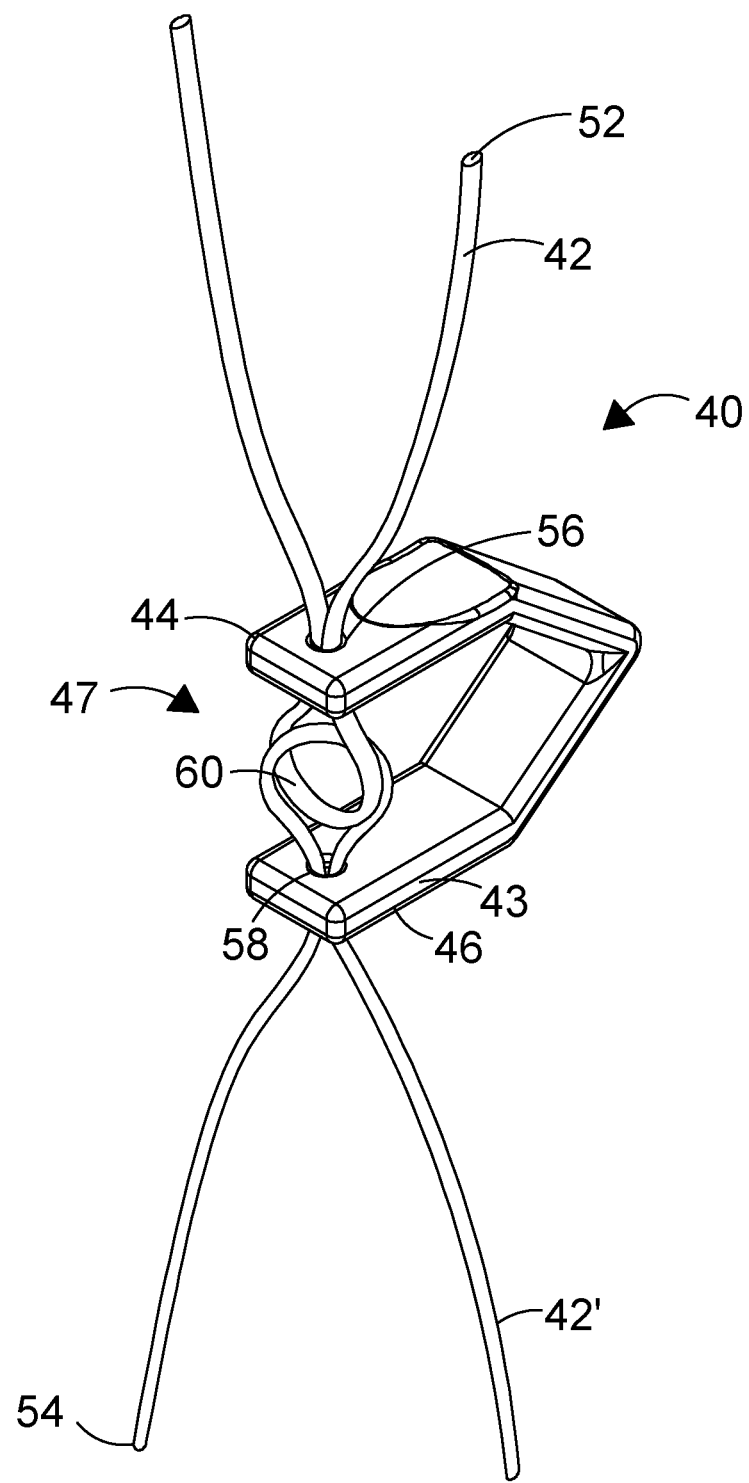
FIG. 4 shows another embodiment of a device of the present invention assembled for use and comprising the compressible operating member with dual intersecting threaded elongate flexible members defining an eye for receiving a vessel (not shown) to be constricted during a surgical procedure, in accordance with an aspect of the present disclosure.

Reference is first made to FIG. 4, which shows an assembled device 40 suitable for controlling fluid through a vessel (not shown) defining a lumen, in accordance with another embodiment. The device 40 comprises an elongate flexible member 42, which in the depicted example is formed from two intersecting threaded elongate flexible members 42, 42' operable together to define an eye 60 of variable dimensions. Each of the elongate flexible members 42, 42' is made from a flexible silicone cord. The elongate flexible members 42, 42' are respectively threaded through arms of a user-compressible operating member 43 illustrated in isolation in FIGS. 3A, 3B, and 3C.

Referring to FIGS. 3A, 3B, and 3C the user compressible operating member 43, in this embodiment is a generally C-shaped member with a proximal hinge portion 48 and first and second arms 44, 46 extending from the proximal hinge portion 48 and having free distal ends. The distal ends of the first and second arms 44, 46 are separated by a gap 47. In the depicted example, the hinge portion 48 is a V- or U-shaped portion of the C-shaped member 43. Each of the first and second arms 44, 46 has a pinhole aperture 61 near the distal end of the respective first and second arms 44, 46. An inner surface 62 defining each pinhole aperture 61 is ribbed in this embodiment to frictionally interact with a portion of the elongate flexible member 42, 42' when threaded through the respective pinhole 61.

As shown in FIG. 4, the compressible operating member 43 receives a pair of elongate flexible members 42, 42', which together function as one to form the elongate flexible member which is configured to form an eye 60 for surrounding the vessel. The eye 60 is located in the gap 47.

The first arm 44 comprises a first threading arrangement 56, and the second arm 46 comprises a second threading arrangement 58. The elongate flexible member 42, 42' is attached to the C-shaped member 43 by threading a first end 52 of the elongate flexible member 42 through the first threading arrangement 56 to form a first loop, and then returning the first end 52 back through the first threading arrangement 56. Then the second elongate flexible member 42' has a free end defined here as the second end 54 that is threaded through the second threading arrangement 58, through the first loop to form a linked second loop and then returning the second end 54 back through the second threading arrangement 58.

In the depicted example, referring again to FIGS. 3A, 3B and 3C each of the first and second threading arrangements 56, 58 is configured as a pinhole aperture 61 which comprises a ribbed inner surface portion 62. Each pinhole aperture therefore forms a plurality of ribs 63 within the pinhole aperture 61 of the C-shaped member 43. In the depicted example, each end of the elongate flexible member 42, 42' is threaded past the ribs 63 of its associated threading arrangement 56, 58. Each portion of the elongate flexible member 42, 42' located in one of the threading arrangements 56, 58 forms a friction fit with the ribbed surface portion 62 within the pinhole aperture 61 of the threading arrangement

56, 58, which allows a portion of the first elongate flexible member 42, 42' located in the gap 47 to be tensioned, and the eye 60 to be biased towards a closed position. The elongate flexible member 42, 42' is threaded through the pinhole aperture 61 of each of the threading arrangements 56, 58 such that in a rest position the portion of the elongate flexible member 42 located in the gap 47 is under tension and the eye 60 may constrict fluid flow through a lumen of a vessel.

Each of the arms 44, 46 is movable inwardly in response to pressure applied to its outer surface. This means that if pressure is applied to one of the arms 44, 46, the portion of the elongate flexible member 42 located in the gap 47 is relaxed, which has the effect of increasing the size of the eye 60, and allowing fluid flow through the lumen. Each of the arms 44, 46 is preferably movable in response to finger pressure applied thereto. An indentation 344, 346 in an outer surface of the respective arms 44, 46 serves as a finger-pressure guide for a user's finger to be applied with reduced risk of slippage off the arm during use of the device 40 in a surgical procedure where body fluids may wet device surfaces thereby interfering with intended use of the device 40.

The at least one elongate flexible member may be formed from a flexible silicone material or a filament which material or filament may be optionally silicone-coated, or at least partially PTFE-coated, which filament may be based on a nylon, a polyester, polypropylene, polyvinylidene fluoride (PVDF) or another flexible material of similar physical properties that is easily manipulated and shaped but is not permanently stretched under tension.

The operating member may be formed from a variety of materials including Acrylonitrile Butadiene Styrene (ABS), nylon, or any other material exhibiting sufficient flexion/flexural modulus which has shape memory and which has shape memory to retain the ability to be repeatably compressed through manipulation by a user. Stainless steel arms, paired and joined or fused at one end, with opposed free ends, and optionally formed with milled gripping holes on the outer surfaces of the arms may be used. Optionally, steamed and formed plywood, impermeably coated with lacquer or a resin would be possible for use in some circumstances but brittle substances such as ceramic or glass would be unsuitable and soft substances such as a synthetic cellular foam or rubber would too flexible, and therefore not suitable for the operating member.

The operating member may be a compressible operating member having curved or angled arms movable towards each other under applied pressure and resiliently revertible when pressure is released, and in particular, compressible when pressure is selectively applied to the operating member by the user. The operating member may be compressible sufficiently to move the distal ends of the arms towards each other in response to finger pressure.

The device may be provided as a part of a kit comprising the device described herein and a prosthetic graft comprising a tubular branch defining a lumen. In such a kit, the device may be provided "ready for use" in that the operating member and elongate flexible members are assembled such that the eye of the device surrounds the branch.

The device disclosed herein may be used in surgical procedures.

The device described herein provides a "fuss free" clip, which uses the same materials as in existing delivery systems, and can be used quickly and efficiently on both natural and synthetic vessels. It is also readily operated by a user intuitively due to its relative simplicity in comparison with several commercially available devices.

The device described herein may be advantageously used to provide haemostasis when different sized catheters are located in the vessel. The medical professional is not required to make any adjustment of the device when a catheter is inserted through the vessel which the device is controlling flow therethrough.

The device described herein provides a simple way for a medical professional to quickly selectively control the flow of fluid through a lumen by applying pressure to the operating member.

The device described herein provides loops which when tightened by pulling, create a smaller though hole or "eye". This interaction between loop and a surface of a vessel around which it is looped, for example a graft with a soft gel weave fabric surface, creates a conformable seal around any device inserted through a lumen in the graft, such as a catheter or sheathing around a device being delivered through the lumen of the graft.

Advantageously, the device may be disassembled and reassembled in situ by the medical professional if required.

The device described in this disclosure is applicable to both natural and synthetic vessels having a length and a transverse dimension defining a lumen or through passage, which vessels may be flexible walled vessels, allowing pinching or constriction applied thereto to close together pinched or constricted wall parts to reduce the transverse dimension of the lumen, additionally permitting closure upon an object such as a catheter within the lumen for example, to form a conformable seal therewith and thereby to completely occlude flow through the lumen when the catheter is in place or whilst it is being removed.

Reference numerals used in the above description of the accompanying drawings are also used in the claims simply for aiding identification of technical features of illustrated embodiments and increasing understanding of the claims without limitation of the scope thereof.

Modifications and improvements may be incorporated without departing from the scope of the invention, which is defined by the appended claims.

As may be recognized by those of ordinary skill in the art based on the teachings herein, numerous changes and modifications may be made to the above-described and other embodiments of the present invention without departing from the scope of the invention. The device for controlling fluid flow through a vessel, the at least one elongate flexible member and the compressible operating member and other components of the device and/or kit as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the device and kit may include more or fewer components or features than the embodiments as described and illustrated herein. For example, the components and features of FIGS. 1-5 may all be used interchangeably and in alternative combinations as would be modified or altered by one of skill in the art. Accordingly, this detailed description of the currently-preferred embodiments is to be taken in an illustrative, as opposed to limiting of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed. The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. A device for controlling fluid flow through a vessel defining a lumen through which fluid may flow, comprising:
   at least one elongate flexible member configured to form an eye for surrounding the vessel defining a lumen, the at least one elongate flexible member having a first attachment point and a second attachment point,
   a compressible operating member attachable to the first attachment point and the second attachment point of said at least one elongate flexible member,
   wherein the compressible operating member has first and second arms separated by a gap, and each of the first and second arms has a distal free end for receiving the at least one elongate flexible member for threading attachment of the at least one elongate flexible member to the first and second arms of the compressible operating member, the compressible operating member being compressible upon the application of pressure to the compressible operating member, and operable to act upon the at least one elongate flexible member such that: the at least one elongate flexible member is movable from a first position in which the at least one elongate flexible member is under tension such that the eye constricts fluid flow within the lumen and a second position in which the at least one elongate flexible member is relaxed such that the eye does not constrict fluid flow through the lumen,
   wherein the at least one elongate flexible member comprises: a first elongate flexible member configured to form a first loop; and a second elongate flexible member configured to form a second loop, wherein the first and second elongate flexible members are configured such that the first and second loops are linked so as to define the eye for surrounding the lumen,
   wherein a portion of the first elongate flexible member comprises the first attachment point and a portion of the second elongate flexible member comprises the second attachment point, wherein the first arm comprises a first threading arrangement, and the second arm comprises a second threading arrangement, and
   wherein the first elongate flexible member is threaded through the first threading arrangement and second elongate flexible member is threaded through the second threading arrangement; and
   wherein the first threading arrangement and the second threading arrangement each comprise an aperture, and an end of the first elongate flexible member is threaded through the aperture in the first threading arrangement sufficiently to provide a length portion of the first elongate flexible member which is formed into a loop and the end of the first elongate flexible member is threaded back through the aperture in the first threading arrangement, and an end of the second elongate flexible member is threaded through the aperture in the second threading arrangement sufficiently to provide a length portion of the second elongate flexible member which is formed into a loop and the end of the second elongate flexible member is threaded back through the aperture in the second threading arrangement, and each flexible member is threaded such that one of the first and second elongate flexible members extends through the loop formed by the other of the first and second elongate flexible members.

2. The device of claim 1, wherein the compressible operating member is compressible upon the application of finger pressure, and the compressible operating member has upper surface and lower surface exterior indentations to facilitate finger pressure.

3. The device of claim 1, wherein the compressible operating member is a C-shaped member,
   wherein the first arm is attachable to the first attachment point, and the second arm is attachable to the second attachment point, and
   wherein the eye is located in the gap.

4. The device of claim 1, wherein the compressible operating member has a proximal V- or U-shaped hinge portion hag wherein the first and second arms extend from the proximal V- or U-shaped hinge portion.

5. The device of claim 1, wherein each aperture has an internal surface which is roughened, or ribbed, or grooved, or serrated to increase frictional interaction with the at least one elongate flexible member.

6. The device of claim 1, wherein the at least one elongate flexible member is formed from a resilient silicone material.

7. The device of claim 6, wherein the at least one elongate flexible member is at least one of a resilient cord or a resilient filament.

8. A kit for use in a surgical procedure comprising the device of claim 1, and a prosthetic graft comprising a tubular branch defining a lumen, wherein (a) the device is provided ready for use in that the compressible operating member and the first and second elongate flexible members of the device are assembled such that the eye of the device surrounds the tubular branch, or (b) the compressible operating member and the first and second elongate flexible members of the device are separate components to be assembled by a user.

9. A kit for use in a surgical procedure comprising a device for controlling fluid flow through a vessel defining a lumen through which fluid may flow, comprising:
   at least one elongate flexible member configured to form an eye for surrounding the vessel defining a lumen, the at least one elongate flexible member having a first attachment point and a second attachment point,
   a compressible operating member attachable to the first attachment point and the second attachment point of said at least one elongate flexible member, wherein the compressible operating member has first and second arms separated by a gap, and each of the first and second arms has a distal free end for receiving the at least one elongate flexible member for threading attachment of the at least one elongate flexible member to the first and second arms of the compressible operating member, the compressible operating member being compressible upon the application of pressure to the compressible operating member, and operable to act upon the at least one elongate flexible member such that: the at least one elongate flexible member is movable from a first position in which the at least one elongate flexible member is under tension such that the eye constricts fluid flow within the lumen and a second position in which the at least one elongate flexible member is relaxed such that the eye does not constrict fluid flow through the lumen, wherein the at least one elongate flexible member comprises: a first elongate flexible member configured to form a first loop; and a second elongate flexible member configured to form a second loop, wherein the first and second elongate flexible members are configured such that the first and second loops are linked so as to define the eye for surrounding the lumen, wherein a portion of the first elongate flexible member comprises the first attachment point and a portion of the second elongate flexible member comprises the second attachment point, wherein the first arm comprises a first threading arrangement, and the second arm comprises a second threading arrangement, and wherein the first elongate flexible member is threaded through the first threading arrangement and second elongate flexible member is threaded through the second threading arrangement; and a prosthetic graft comprising a tubular branch defining a lumen, wherein (a) the device is provided with the compressible operating member and the first and second elongate flexible members of the device are assembled such that the eye of the device surrounds the tubular branch, or (b) the compressible operating member and the first and second elongate flexible members of the device are separate components to be assembled by a user.

* * * * *